United States Patent [19]

Käss

[11] Patent Number: 5,502,201

[45] Date of Patent: Mar. 26, 1996

[54] PROCESS FOR PREPARING 2-CHLORO-BENZOTHIAZOLES OR 2-CHLORO-BENZOXAZOLES

[75] Inventor: Volker Käss, Leverkusen, Germany

[73] Assignee: Bayer Aktiengesellschaft, Leverkusen, Germany

[21] Appl. No.: 230,177

[22] Filed: Apr. 20, 1994

[30] Foreign Application Priority Data

Apr. 27, 1993 [DE] Germany ............ 43 13 748.2
Apr. 27, 1993 [DE] Germany ............ 43 13 750.4

[51] Int. Cl.⁶ .................. C07D 277/68; C07D 263/54
[52] U.S. Cl. ............................. 548/152; 548/217
[58] Field of Search .................... 548/152, 217

[56] References Cited

U.S. PATENT DOCUMENTS

| | | |
|---|---|---|
| 2,469,697 | 5/1949 | Moon . |
| 3,284,294 | 11/1966 | Sasse et al. . |
| 4,229,565 | 10/1980 | Gardner ........................ 528/176 |
| 4,334,073 | 6/1982 | Diehr . |
| 4,509,971 | 4/1985 | Forster et al. . |
| 4,517,370 | 5/1985 | Becherer et al. . |
| 4,833,243 | 5/1989 | Forster et al. . |

FOREIGN PATENT DOCUMENTS

| | | |
|---|---|---|
| 213291 | 2/1984 | Czechoslovakia . |
| 1210617 | 2/1966 | Germany . |
| 1670453 | 2/1971 | Germany . |
| 3207153 | 9/1983 | Germany . |
| 3234531 | 3/1984 | Germany . |

OTHER PUBLICATIONS

Chemical Abstracts, vol. 43, Aug. 25, 1949, No. 16, 6670, 1 page. "2–Chlorobenzothiazole", N.S. Moon, USP 2,469,697.
Chemical Abstracts, vol. 101, Aug. 27, 1984, No. 9, p. 644; CA#72718s: "2–Chlorobenzothiaole"; Czech Patent 213, 291.
Japanese Chemical Abstract, FARB, CO2, 86262B/48=J5 4154–762; "2–carbamoyl:methoxy–benzoxazole and benzothiazole . . . " Bayer AG, Feb. 2, 1979. (1 page).

*Primary Examiner*—Robert Gerstl
*Attorney, Agent, or Firm*—Sprung Horn Kramer & Woods

[57] ABSTRACT

The title compounds of the formula

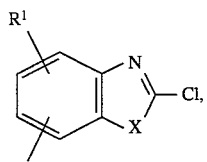
(I)

in which $R^1$ and $R^2$, independently of one another, represent hydrogen, straight-chain or branched $C_1$-$C_4$-alkyl, straight-chain or branched $C_1$-$C_4$-alkoxy, nitro, fluorine, chlorine, bromine, $SO_2Cl$, cyano or $SO_2$-$C_1$-$C_4$-alkyl, and X represents sulphur or oxygen, can be prepared from the corresponding 2-mercapto-benzothiazoles or 2-mercapto-benzoxazoles by chlorination with thionyl chloride in the presence of phosphorous acid compounds of the formula $$YP(OR^5)_2 \quad \quad (III),$$

in which $R^5$ represents hydrogen, straight-chain or branched, substituted or unsubstituted $C_1$-$C_{12}$-alkyl, phenyl or $C_7$-$C_{10}$-aralkyl and Y represents hydrogen or $OR^5$.

9 Claims, No Drawings

PROCESS FOR PREPARING 2-CHLORO-BENZOTHIAZOLES OR 2-CHLORO-BENZOXAZOLES

The present invention relates to a process for preparing the title compounds from the corresponding 2-mercapto compounds and thionyl chloride in the presence of phosphorous acid compounds and also to a process for isolating elemental sulphur from the resulting liquid reaction mixtures. The process of the invention is carried out at a temperature of 30°–140° C.

The title compounds are, in substituted or unsubstituted form, important intermediates, for example for preparing active compounds in the crop protection area or for dyes. Thus, 2-chloro-benzothiazole is an intermediate for the preparation of herbicides (EP-B1-0 005 501; EP-A1- 0 014 409).

German Offenlegungsschrift 1 670 453 discloses the preparation of 2-chloro-benzothiazole, which may be substituted by halogen or nitro, from the corresponding 2-mercapto-benzothiazole or the disulphide thereof by reaction with chlorine in the presence of inert organic solvents at a moderately elevated temperature of 70°–150° C. or more advantageously at 80°–90° C. The examples of German Offenlegungsschrift '453 give yields of 79.5–87% of the theoretical yield of 2-chloro-benzothiazole.

A further process for preparing 2-chloro-benzothiazole by chlorination of 2-mercapto-benzothiazole according to German Offenlegungsschrift 3 234 531 is characterized by the use of phosphorus trichloride and elemental chlorine as chlorination agent and a tertiary amine as catalyst. According to this process, the yields can be increased to about 92% of the theoretical yield, but this process is very complicated in its execution and in the work-up of the reaction mixture. Finally, it is known from Houben-Weyl, Methoden der organischen Chemie, Volume V/3, p. 871, that 2-mercapto-benzothiazole can be reacted as a slurry in excess phosphorus oxychloride or phosphorus trichloride with thionyl chloride to give 2-chlorobenzothiazole.

It has now been found that the chlorination of the corresponding 2-mercapto compounds to the title compounds can be carried out with thionyl chloride in conventional and easy-to-handle organic solvents and diluents if the reaction is carried out in the presence of a small amount of a phosphorous acid compound.

A process has been found for preparing 2-chlorobenzothiazoles or 2-chloro-benzoxazoles of the formula (I)

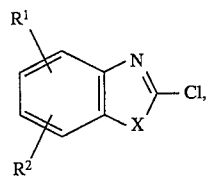

in which
$R^1$ and $R^2$, independently of one another, represent hydrogen, straight-chain or branched $C_1$-$C_4$-alkyl, straight-chain or branched $C_1$-$C_4$-alkoxy, nitro, fluorine, chlorine, bromine, $SO_2Cl$, cyano or $SO_2$-$C_1$-$C_4$-alkyl, and
X represents sulphur or oxygen,
by chlorination of 2-mercapto-benzothiazoles or 2-mercapto-benzoxazoles of the formula

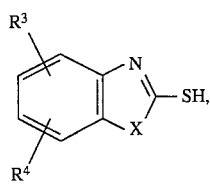

in which
$R^3$ and $R^4$, independently of one another, can have any of the meanings given for $R^1$ and $R^2$ and can additionally and independently of one another denote $SO_3H$,
with thionyl chloride, which is characterized in that the chlorination is carried out using 0.8–3 mol of $SOCl_2$ per mol of the 2-mercapto compound in the temperature range of 30°–140° C. and in a reaction medium of 50–1000% by weight, based on the 2-mercapto compound, of a solvent or diluent and also using 0.001–5 mol %, based on the 2-mercapto compound, of a phosphorous acid compound of the formula $$YP(OR^5)_2 \quad (III),$$

in which
$R^5$ represents hydrogen, straight-chain or branched $C_1$-$C_{12}$-alkyl which may be mono- or disubstituted by halogen and/or $C_1$-$C_4$-alkoxy, phenyl which may be mono- or disubstituted by halogen and/or $C_1$-$C_4$-alkyl and/or $C_1$-$C_4$-alkoxy, or $C_7$-$C_{10}$-aralkyl which may have its aromatic part mono- or disubstituted by halogen and/or $C_1$-$C_4$-alkyl and/or $C_1$-$C_4$-alkoxy, although in the case of disubstitution the substituents present may be identical or different, and
Y represents hydrogen or $OR^5$.

Straight-chain or branched $C_1$-$C_4$-alkyl is, for example, methyl, ethyl, propyl, isopropyl, butyl, isobutyl, preferably methyl or ethyl, particularly preferably methyl. Straight-chain or branched $C_5$-$C_{12}$-alkyl is one of the isomeric pentyls, hexyls, octyls, decyls or dodecyls.

Straight-chain or branched $C_1$-$C_4$-alkoxy is, for example, methoxy, ethoxy, propoxy, isopropoxy, butoxy, isobutoxy, preferably methoxy or ethoxy, particularly preferably methoxy.

$C_1$-$C_4$-alkyl in the substituent $SO_2$-$C_1$-$C_4$-alkyl has the abovementioned meaning.

$C_7$-$C_{10}$-aralkyl is, for example, benzyl, α- and β-phenyl-ethyl, phenyl-propyl or phenyl-butyl, preferably benzyl.

Alkyl, phenyl or aralkyl may be mono- or disubstituted by halogen, such as fluorine, chlorine or bromine, preferably chlorine, by $C_1$-$C_4$- alkyl or $C_1$-$C_4$-alkoxy. In the case of disubstitution, the two substituents may also be different.

In a preferred form, the compounds chlorinated are 2-mercapto compounds of the formula

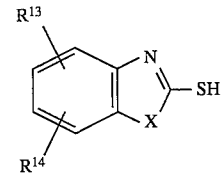

in which
$R^{13}$ and $R^{14}$, independently of one another, represent hydrogen, methyl, ethyl, methoxy, ethoxy, fluorine or chlorine and
X represents sulphur or oxygen.

In a particularly preferred embodiment of the process of the invention, the 2-mercapto compounds have the formula

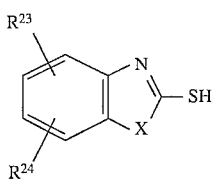

(V)

in which $R^{23}$ and $R^{24}$, independently of one another, represent hydrogen, methyl or chlorine and X represents sulphur or oxygen.

In a further preferred embodiment of the process of the invention, the compounds reacted are 2-mercapto compounds, in which X represents sulphur.

In a further preferred embodiment of the process of the invention, the compounds reacted are 2-mercapto compounds in which the benzene ring bears only one substituent.

Preferred phosphorous acid compounds for the process of the invention are those in which Y represents $OR^5$.

Particularly preferred phosphorous acid compounds for the process of the invention are those of the formula $$P(OR^{15})_3 \qquad (VI),$$

in which $R^{15}$ represents hydrogen, straight-chain or branched $C_1$-$C_{12}$-alkyl, phenyl, chlorophenyl, tolyl or benzyl.

The process of the invention can, for the example of the reaction of unsubstituted mercapto-benzothiazole, be depicted in formulae as follows:

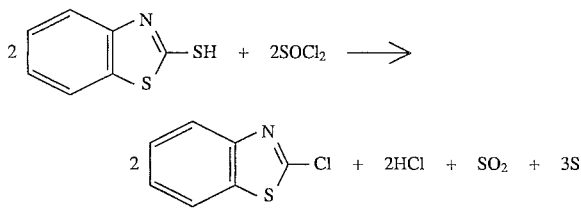

The process of the invention can be carried out with an amount of thionyl chloride of 0.8–3 mol, preferably 0.9–1.5 mol, particularly preferably 1–1.2 mol, per mol of the 2-mercapto compound. If thionyl chloride is used in an amount below the lower limit of 0.8 mol, this involves the risk of incomplete conversion. If thionyl chloride is used in an amount above the upper limit of 3 mol, this is possible in principle, but necessitates the recycling of a major amount of unconsumed thionyl chloride and produces unnecessarily large amounts of sulphur as residue.

The above-described phosphorous acid compound is used, according to the invention, in an amount of 0.001–5 mol %, preferably 0.001–1 mol %, particularly preferably 0.01–0.8 mol %, based on the 2-mercapto compound.

Solvents or diluents for the process of the invention are, for example, (cyclo) aliphatic and aromatic (halogeno) hydrocarbons, such as $C_5$-$C_{12}$-aliphatics, mixtures thereof such as ligroin, petroleum ether, benzine, kerosene; benzene, toluene, xylene; methylene chloride, chloroform, carbon tetrachloride, chlorinated $C_2$-$C_8$-aliphatics, and also brominated and fluorinated analogues, chlorobenzene, dichlorobenzene, trichlorobenzene, chlorotoluene, dichlorotoluene, chloroxylene and brominated and fluorinated analogues and also mixtures thereof, with chlorinated hydrocarbons being preferred among the halogenated hydrocarbons; esters, ethers, nitro-aromatics, such as ethyl acetate, butyl acetate and analogous propionates and buryrates, diethyl ether, methyl butyl ether, methyl tert-butyl ether (MTBE), tetrahydrofuran, dioxane, nitrobenzene, nitrotoluene and analogues known to those skilled in the art; ketones such as acetone, methyl ethyl ketone and others. Finally, the reaction product itself can be employed as solvent or diluent for the system, provided that it is liquid at the reaction temperature.

Solvents or diluents or a mixture of a plurality thereof are used in an amount of 50–1000% by weight, preferably 70–700% by weight, particularly preferably 80–500% by weight, based on the 2-mercapto compound.

The process of the invention is carried out in the temperature range of 30°–140° C. Preferably, the temperature is first, until about the addition of an equimolar amount of $SOCl_2$, maintained in the range of 30°–70° C., particularly preferably in the range of 50°–65° C.; then the temperature is raised into the range of 60°–140° C., preferably 70°–120° C. The pressure is, in principle, not critical; with low-boiling solvents or diluents increased pressure may be applied to maintain a liquid phase.

The work-up of the reaction mixture is carried out by fractional distillation, initially at atmospheric pressure and then in vacuo.

The starting 2-mercapto compounds have very poor solubility in many solvents. Processes of the prior art attempted to overcome this situation soon after the beginning of the reaction by selection of particular reaction media. In contrast, in the process of the invention the reaction mixture is heterogeneous for a long time, almost until completion of the chlorination. Yet, sufficient reactivity is surprisingly ensured, which allows inert and easily handled solvents or diluents to be used.

The process of the invention allows the preparation of the title compounds in high yields and high purity. Thus, for example, unsubstituted 2-chloro-benzothiazole is obtained on work-up by distillation in a purity of over 99% in the main fraction and, taking all further recyclable fractions into account, in a total yield of up to 95%.

The zero-valent, elemental sulphur produced in large amounts in the reaction is formed by comproportionation. Frequently, elemental sulphur formed in such reactions is obtained in the form of finely-divided, sometimes even colloidal, sulphur which is difficult to filter and thus severely interferes with the work-up in most cases. Furthermore, all work-up residues containing elemental sulphur are associated with organic impurities which generally allow disposal to be carried out only by incineration. In such a case, the sulphur is obtained as $SO_2$ and, in accordance with present-day ecological understanding, has to be disposed of by means of flue gas desulphurization, forming gypsum in amounts and qualities which frequently make further use questionable.

It has now been found that the elemental sulphur can be isolated in crystalline form if, in the work-up of the reaction mixture by distillation, this distillation is conducted in such a way as to obtain and maintain a liquid distillation residue whose liquid state, with the exception of the crystallizing sulphur, is maintained even on cooling.

The invention accordingly also provides a process for isolating elemental sulphur from liquid reaction mixtures which are formed by reaction of mercapto compounds with thionyl halides in an organic solvent, which is characterized in that after at least part of the distillable components have been removed by distillation, leaving a likewise liquid distillation residue, this distillation residue is cooled by 20°–120° C., preferably by 30°–100° C., while maintaining its liquid state, with the exception of the sulphur which crystallizes out, and the sulphur which has crystallized out is separated off mechanically.

This process of the invention can in principle be applied to all mercapto compounds from which the corresponding halogen compound is prepared by reaction with a thionyl halide such as thionyl chloride or thionyl bromide, preferably thionyl chloride. This reaction is important, in particular, in all cases where the synthesis of the starting materials has resulted in the presence of a mercapto group which is then to be converted into a halogeno group. This is the case for heterocycles in particular and here particularly for benzothiazole and benzoxazole compounds.

To obtain elemental sulphur, therefore, the mercapto compounds used are preferably 2-mercapto-benzothiazoles and 2-mercapto-benzoxazoles of the formula

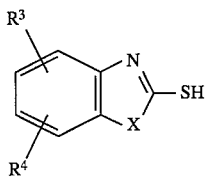

(I)

in which $R^3$ and $R^4$, independently of one another, represent hydrogen, straight-chain or branched $C_1$-$C_4$-alkyl, straight-chain or branched $C_1$-$C_4$-alkoxy, nitro, fluorine, chlorine, bromine, $SO_2Cl$, $SO_3H$, cyano or $SO_2$-$C_1$-$C_4$-alkyl and X represents sulphur or oxygen.

Further preferred embodiments for obtaining elemental sulphur of the mercapto compounds used, to those employed for preparing the preferred title compounds.

Suitable solvents or diluents for the reaction mixtures to be treated according to the invention also include for the purpose of isolating sulphur, besides those already specified above, the following: acetonitrile; lower dialkyl carbonates such as dimethyl carbonate; peralkylated acid amides such as dimethylformamide (DMF), dimethylacetamide (DMA), N-methyl-pyrrolidone (NMP), N-methyl-caprolactam (NMC); N-substituted morpholines; phosphorus halides such as phosphorus oxychloride, phosphorus trichloride; further solvents known to those skilled in the art from the reference literature, provided that they are liquid and inert at the reaction temperature of the chlorination and the subsequent treatment according to the invention.

In a preferred form, the solvents or diluents used are the abovementioned aliphatic and aromatic (halogeno)hydrocarbons, esters, ethers, nitroaromatics, particularly preferably aliphatic and aromatic (halogeno)hydrocarbons.

The reaction mixtures to be treated according to the invention for obtaining elemental sulphur can also contain reaction accelerators such as tertiary amines, phosphites or others. Preferred accelerators of this type are the abovementioned phosphorous acid compounds of the formula (III) and their further preferred embodiments.

For the reaction mixtures prepared for the purpose of obtaining sulphur, such phosphites are generally used in an amount of 0.01–5 mol %, preferably 0.02–1 mol %, particularly preferably 0.04–0.8 mol %, based on the mercapto compound. The halogenation of the mercapto compound with thionyl halide in the presence of such a phosphite is carried out, for example, in the temperature range of 30°–140° C.

The reaction mixture to be worked up according to the invention for obtaining elemental sulphur is treated by distillation. In this procedure, excess thionyl halide and solvent are first removed in a first fraction, after which, with improved vacuum, the distillative isolation of the halogenated product derived from the mercapto compound is carried out. According to the prior art, this results in a distillation bottom product which on cooling becomes a viscous mass which partly solidifies. For easier handling of this distillation bottom product, for example for feeding to an incineration plant with flue gas desulphurization, this distillation bottom product is preferably and at the required cost maintained in the liquid state at elevated temperature so that it can be conveyed by pumps into an incineration plant.

According to the invention, the reaction mixture to be worked up is freed by distillation from at least part of the distillable components and is subsequently cooled by 20°–120° C., preferably by 30°–100° C., with the sulphur precipitating in crystalline form. In this process, the distillation residue has to remain liquid, with the exception of the sulphur which crystallizes out. This can be achieved, for example, by two variants:

a) From the reaction mixture, any unreacted thionyl halide and the solvent or a mixture of a plurality thereof are first taken off as a first fraction and then the halogenated product derived from the mercapto compound is taken off as the main fraction. The distillation bottom product, still hot, is then diluted with a solvent of the abovementioned type, for example with the first fraction. For this purpose, in a preferred embodiment, the first fraction is used in an amount of 50–100% of the total amount thereof, preferably 80–100% of the total amount thereof. It is of course possible to add further solvent, in addition to the first fraction, to the hot distillation bottom product. In general, this is only used to compensate for losses of solvent. After cooling to the abovementioned temperature range, the sulphur which has crystallized out can be separated off mechanically, for example by crystallization, decantation, centrifugation or by similar operations. The crystalline sulphur which has been mechanically separated off is then washed with solvent or with water and can, after drying, be supplied to an industrial application, for example sulphuric acid production. In this way, sulphur having a purity above 98% can be isolated in an amount of more than 80% of the total sulphur present in the distillation bottom product. The mother liquor obtained from the mechanical separation of the crystalline sulphur consists essentially of the solvent used, for example the distillation first fraction used, and further contains added reaction accelerators, such as an abovementioned phosphite, and also residual reaction product and any unreacted mercapto compound and can be added in this form as solvent or diluent to the next batch for the halogenation of further mercapto compounds. Depending on the solubility conditions, it can further contain residual sulphur which has not crystallized out.

b) A reaction batch from the halogenation of a mercapto compound is distillatively freed of only a first fraction, comprising unreacted thionyl halide and the solvent, and optionally an intermediate fraction. The remainder of the reaction mixture thus treated, which still contains the halogenated reaction product derived from the mercapto compound, is then cooled to a temperature in the abovementioned range, whereupon, in this variant too, sulphur precipitates in crystalline form. After mechanically separating off the sulphur in the abovementioned form, the remainder of the reaction mixture obtained as mother liquor is further treated by distillation, which gives the halogenated reaction product (in general in a vacuum distillation) and now only a small amount of a distillation bottom product which has been largely freed of sulphur. This small amount of distillation bottom product now causes considerably lower expense with regard to both its reduced amount and also its greatly reduced sulphur content and the necessity of flue gas desulphurization.

The process of the invention is a significant contribution to reducing environmental pollution by chemical residues in that a but insignificant distillation saves significantly higher expenditure on energy and efforts to achieve other forms of residue disposal.

The cooling of the reaction mixture concentrated by distillation can, for example, be carried out down to a temperature range of 40°–70° C., preferably 45°–55° C. This temperature range has proven to be advantageous with the use of halogenoaromatics as solvents. In all cases, the favourable range is dependent on the boiling point of the solvent and on the commencement of crystallization of the sulphur and is determined by routine preliminary experiments.

EXAMPLE 1

A 4 l four-necked flask was fitted with stirrer, thermometer, condenser and dropping funnel having a long immersed tube. 489 ml=802.8 g (6.7 mol) of $SOCl_2$ were introduced via the immersed tube into an initially charged suspension of 1017.9 g of 2-mercapto-benzothiazole (6 mol) and 3.5 g of triphenyl phosphite in 1200 ml=1320 g of chlorobenzene over a period of about 6 hours at 60°–65° C. The measured addition rate here followed the strong gas evolution. The suspension, which was very thick initially, only became thinner and easier to stir in the course of the $SOCl_2$ addition; at the end a solution was present. After addition of the $SOCl_2$, the mixture was stirred for a further 3 hours at 90° C. A fractional distillation was then carried out, starting at atmospheric pressure and continued at reduced pressure, to isolate chlorobenzene and the 2-chloro-benzothiazole (2-CBT) which boils at about 140° C./35 mbar. The following conditions were set; the following results were obtained:

|  | Bottom | Top | Heating bath | Pressure |
| --- | --- | --- | --- | --- |
| First fraction | up to 120° C. | up to 70° C. | up to 144° C. | from 1000 to 25 mbar |
| Intermediate fraction | up to 134° C. | up to 122° C. | up to 162° C. | 25 mbar |
| Main fraction | up to 208° C. | 125–70° C. | up to 220° C. | 20 mbar |

The waste gas from the reaction was passed into dilute sodium hydroxide solution. The residue contained, besides the elements C, H, N, Cl, O and P, about 76% by weight of sulphur. The residue was drained from the flask at a temperature of about 100° C.; the flask was rinsed with 100 ml of o-dichlorobenzene and thus cleaned for the next batch. Repeating the reaction with o-dichlorobenzene as solvent/diluent gave comparable results.

EXAMPLE 2

The residue diluted with o-dichlorobenzene from Example 1 was incinerated in a residue disposal plant equipped with flue gas desulphurization.

EXAMPLE 3

Example 1 was repeated, but leaving the distillation residue in the distillation flask. After cooling this distillation bottom product to about 120°–130° C., the whole of the previously removed first fraction was added and the mixture thus combined was cooled to 45°–50° C. This resulted in the crystallizing out of sulphur which was filtered off and subsequently washed three times with 50 ml of chlorobenzene. After drying, 260 g of sulphur having a purity of 98.7% were obtained. The mother liquor obtained was added as solvent simultaneously containing the reaction accelerator phosphite to the next reaction bath, and comparable results were obtained.

EXAMPLE 4

Example 1 was repeated, except that only the solvent was removed from the reaction mixture as first fraction. And for this the distillation was carried out only up to a bottom temperature of 120° C. and a vacuum of up to 200 mbar. The reaction mixture freed of the first fraction was then, as indicated in Example 3, cooled to 45°–50° C. and freed of the sulphur, which crystallized out, in the manner indicated in Example 3. The mother liquor obtained was combined with the chlorobenzene used for washing the sulphur filtered off and again subjected to a distillation in which, after taking off an intermediate fraction, the main fraction indicated in Example 1 was obtained. The then remaining distillation bottom product comprised 96.5 g and thus only about ¼ of the distillation bottom product obtained in Example 1.

I claim:

1. A process for preparing 2-chloro-benzothiazoles or 2-chloro-benzoxazoles of the formula

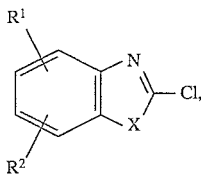

in which

R¹ and R², independently of one another, represent hydrogen, straight-chain or branched $C_1$-$C_4$-alkyl, straight-chain or branched $C_1$-$C_4$-alkoxy, nitro, fluorine, chlorine, bromine, $SO_2Cl$, cyano or $SO_2$-$C_1$-$C_4$-alkyl, and X represents sulphur or oxygen, which comprises chlorinating with thionyl chloride 2-mercapto-benzothiazoles or 2-mercapto-benzoxazoles of the formula

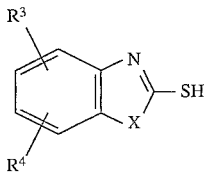

in which

R³ and R⁴, independently of one another, have the same meanings given for R¹ and R² or independently of one another denote $SO_3H$ wherein said chlorination is carried out at a temperature range of 30° to 140° C. and in the presence of 50–1000% by weight based on the 2-mercapto compound of a solvent or diluent and comprises 0.8–3- mol of $SOCl_2$ per mole of the 2-mercapto compound; and 0.001–5 mol %, based on the 2-mercapto compound, of a phosphorous acid compound of the formula

in which

R[5] represents hydrogen, straight-chain or branched $C_1$-$C_{12}$-alkyl which is unsubstituted or mono- or disubstituted by halogen and/or $C_1$-$C_4$-alkoxy, phenyl which is optionally mono- or disubstituted by halogen and/or $C_1$-$C_4$-alkyl and/or $C_1$-$C_4$-alkoxy, or $C_7$-$C_{10}$-aralkyl wherein its aromatic part is optionally mono- or disubstituted by identical or different substituents wherein the substituents are halogen and/or $C_1$-$C_4$-alkyl and/or $C_1$-$C_4$-alkoxy and Y represents hydrogen or OR[5].

2. Process according to claim 1, wherein the 2-mercapto-benzothiazoles or 2-mercapto-benzoxazoles chlorinated have the formula

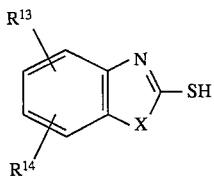

in which

R[13] and R[14], independently of one another, represent hydrogen, methyl, ethyl, methoxy, ethoxy, fluorine or chlorine and X represents sulphur or oxygen.

3. Process according to claim 1, wherein the 2-mercapto compound bears only one substituent.

4. Process according to claim 1, wherein X represents sulphur.

5. Process according to claim 1, wherein 0.9–1.5 mol, of $SOCl_2$ are used per mole of 2-mercapto compound.

6. Process according to claim 1, wherein the phosphorous acid compound used has the formula $P(OR^{15})_3$, in which R[15] represents hydrogen, straight-chain or branched $C_1$-$C_4$-alkyl, phenyl, chlorophenyl, tolyl or benzyl.

7. Process according to claim 1, wherein 70–700% by weight, based on the 2-mercapto compound, of solvent or diluent are used.

8. Process according to claim 1, wherein the solvent or diluent is one or more from the group of the aliphatic, cycloaliphatic or aromatic hydrocarbons, of the halogenated, aliphatic, cycloaliphatic or aromatic hydrocarbons, of the esters, ethers or of the nitroaromatics which are liquid in the range of the reaction temperatures.

9. Process according to claim 1, wherein the reaction is carried out in the temperature range of 50°–120° C.

* * * * *